United States Patent
Lutz et al.

(10) Patent No.: US 7,527,626 B2
(45) Date of Patent: May 5, 2009

(54) EXTERNAL FIXATION ELEMENT

(75) Inventors: Christian Lutz, Solothurn (CH); Vinzenz Burgherr, Bern (CH); Olivier Palefroy, Villard (FR)

(73) Assignee: Stryker Trauma SA (CH)

( * ) Notice: Subject to any disclaimer, the term of this patent is extended or adjusted under 35 U.S.C. 154(b) by 0 days.

(21) Appl. No.: 10/959,340

(22) Filed: Oct. 5, 2004

(65) Prior Publication Data
US 2005/0085810 A1    Apr. 21, 2005

(30) Foreign Application Priority Data
Oct. 6, 2003  (EP)  ................................. 03405713

(51) Int. Cl.
*A61B 17/56* (2006.01)
(52) U.S. Cl. ..................................... 606/54
(58) Field of Classification Search ............. 606/54, 606/59, 61, 64, 70, 76, 97, 298, 331; 600/414, 600/415
See application file for complete search history.

(56) References Cited

U.S. PATENT DOCUMENTS

| | | | |
|---|---|---|---|
| 4,258,708 A | | 3/1981 | Gentile |
| 4,365,624 A | * | 12/1982 | Jaquet ........................ 606/56 |
| 4,738,248 A | * | 4/1988 | Ray ........................... 600/206 |
| 5,181,930 A | | 1/1993 | Dumbleton et al. |
| 5,443,513 A | | 8/1995 | Moumene et al. |
| 5,591,164 A | | 1/1997 | Nazre et al. |
| 6,045,553 A | | 4/2000 | Iversen et al. |
| 6,080,153 A | * | 6/2000 | Mata et al. ..................... 606/54 |
| 6,325,802 B1 | * | 12/2001 | Frigg .......................... 606/61 |
| 6,379,362 B1 | | 4/2002 | Birk et al. |
| 6,506,972 B1 | * | 1/2003 | Wang .......................... 174/36 |
| 2003/0149429 A1 | | 8/2003 | Ferrante et al. |
| 2004/0116925 A1 | | 6/2004 | Gill et al. |

FOREIGN PATENT DOCUMENTS

| | | |
|---|---|---|
| CH | 303453 | 2/1955 |
| EP | 717 968 A2 | 6/1996 |
| FR | 2 338 692 | 8/1977 |

\* cited by examiner

*Primary Examiner*—Eduardo C Robert
*Assistant Examiner*—David Comstock
(74) *Attorney, Agent, or Firm*—Lerner, David, Littenberg, Krumholz & Mentlik, LLP

(57) ABSTRACT

An external fixation system has clamps, rods and pins having anti-magnetic core parts and a non-conductive sheath part covering essentially the exterior surfaces of the core part. The rods, pins and clamps are especially MRI safe for a patient when used in any frame configuration for fractures of the upper and lower extremities and pelvis wherein the usual MRI field parameters of a static field of 2 Tesla, a time-varying filed of max. 20 Tesla/sec and a specific absorption rate (SAR) of max. 0.4 Watts/kg averaged over the whole body of the patient apply.

25 Claims, 2 Drawing Sheets

EXTERNAL FIXATION ELEMENT

BACKGROUND OF THE INVENTION

This invention relates to external fixation elements, especially to external fixation rods. More particularly, it relates to an apparatus and method to make use of such elements safer during MRI procedures.

Magnetic Resonance Imaging (MRI) is a well known diagnostic tool in the field of medicine. It is equally known to surgeons that problems may occur for patients wearing metallic devices inside or outside their body during examination with a MRI device (inside or outside the coil).

It is known in the prior art, e.g. from FR 2 703 580, to use antimagnetic implants, e.g. made in polyethylene, and to use additional radiopaque markers to get an image of the implant. This makes such an implant MRI-safe.

U.S. Publication No. 2002/042619 discloses a headframe for use with a stereotactic system. It is mentioned in the last paragraph of the description that the frame body and swivel arms need not to be made from aluminum. Instead, the frame body and swivel arms as well as other components of the headframe may be formed of a non-magnetic material such as plastic, ceramic, or other composite such that the headframe is compatible with MRI, CT, X-ray and magnetic stereotactic device/procedures.

In the field of elements constituting an external fixation device or to be used with an external fixation device it is known to use rods of, for example, stainless steel. However, the use of such ferromagnetic rods does not allow MRI examinations. As an alternative, rods of aluminum or of carbon fibers may be used. Rods made from the latter named materials are not ferromagnetic. However, within the field of external fixation, the combination of these elements, e.g. rods with clamps and pins, constitute either along or together with the body of the patient a closed conductive loop.

For MRI safety, it is equally important not to interfere with the static field, the gradient field as well as the RF-field, therefore such external fixation elements cannot be used in MRI environments.

SUMMARY OF THE INVENTION

In view of this prior art, one aspect of the invention is to provide external fixation elements, wherein a patient carrying such a structure can safely be examined within a MRI device.

During MRI scanning, critical heat can be generated in such external fixation frames that can cause burns, necrosis or nerve stimulation in the tissue of the human body. Furthermore, a torque may be generated resulting in a vibration or movement of the device.

It is another aspect of the invention to provide external fixation elements with the least possible magnetic field interactions (i.e. deflection and/or torque), heating and nerve stimulation.

It is yet a further aspect of the invention to limit artifacts in the generated MRI images due to the external fixation elements.

The field strength, i.e. the highest strength of the static magnetic field of a MRI system, is often between 1.5 Tesla and 3.0 Tesla, more often around 2.0 Tesla. However, elements according to the invention can also be used in association with very high-field-strength MRI systems having a field strength of up to 8.0 Tesla.

These and other aspects of the invention are achieved by a MRI safe external fixation system having at least two rod clamps made of an electrically conductive non-ferromagnetic material. The clamps have a non-electrically conductive insulation covering and are connected by at least one rod extending between the clamps. The rod is made from a non-ferromagnetic material core surrounded by a non-electrically conductive sheath. The clamps engage the rod in such a manner that torsion applied to the rod tending to rotate the rod within the clamps causes slippage between the clamp and the sheath of the rod before any slippage occurs between the sheath and the core itself.

Preferably, the core is made of metal and the sheath is made from a polymeric or resin material which acts an electrical insulator with the sheath being bonded to an outer circumferential surface of the rod core.

BRIEF DESCRIPTION OF THE DRAWINGS

Further objects and advantages are achieved through the features of the subclaims and exemplary embodiments of the invention are disclosed in the following description in which:

DETAILED DESCRIPTION

Figure 1:
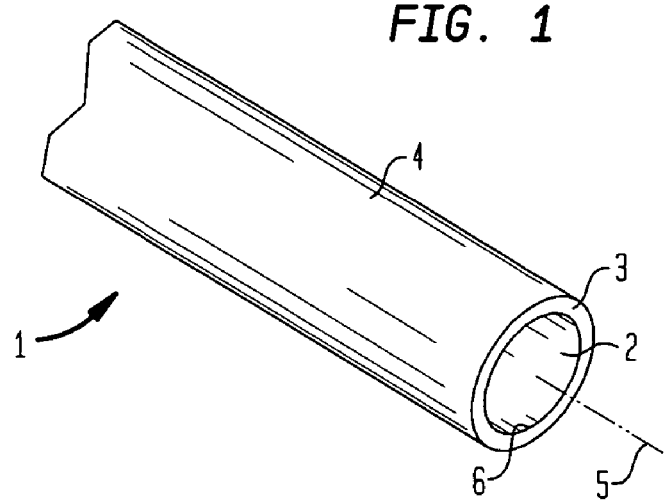
FIG. 1 is a schematic view of a rod according to the invention for use in an external fixation device.

FIG. 1 shows a schematic view of rod 1 for use in an external fixation device. The core has received the reference numeral 2. A non-conductive sheath 3 encloses the core 2. The cylindrical surface 4 of the sheath may be smooth or comprise a grid of high spots. Preferably rod 1 is available with different diameters depending on its use in an external fixation device, e.g. as thicker rods 1 and thinner pins 30 as shown in FIG. 2.

Figure 2:
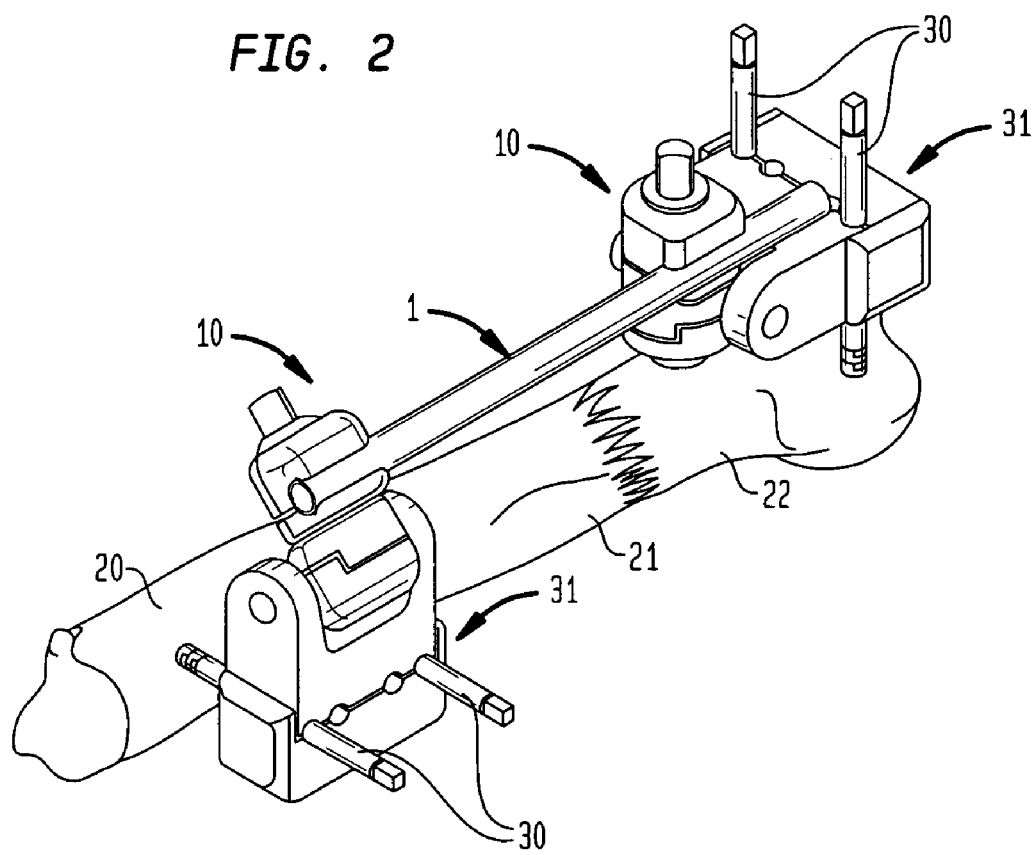
FIG. 2 is a view of several fixation elements according to the invention with a rod according to FIG. 1.

The rod 1 according to the invention is to be used with further elements of an external fixation system or frame, e.g. clamps 10 and 31 as shown in FIG. 2. FIG. 2 shows a schematic view of the use of an external fixation system with a broken bone 20 using several fixation elements according to the invention. Pins 30 are drilled into the bone parts 21 and 22, respectively and held within clamp parts 31. The clamp parts 31 are mounted together with clamps 10. The two clamps 10 are connected via the rod 1 oriented mainly in parallel to the broken limb 21, 22.

The clamps 10 and 31 can be made of titanium. Such clamps 10 are then non-ferromagnetic but electrically conductive. However, the use of such conductive clamps 10 and 31 does not close the external fixation frame to a closed electrical loop, since the rods 1 are not conductive. Therefore, the combination of the disclosed rods 1 from an anti-ferromagnetic material with clamps 10 and 31 and pins 30 are MRI-safe. There are almost no induced currents. The use of the non-conductive elements 1 disrupts the closed loop usually formed by rod 1, clamp parts 10 and 31, pin 30 and the human body, here represented through the bone parts 21 and 22. The use of non-magnetic material for clamp 31 also disrupts the smaller loop formed by the two pins 30 together with one clamp part 31 and the bone.

Beside the use of conductive pins 30, it is in principle possible to use shielded or non-conductive materials for pins 30.

Figure 3:
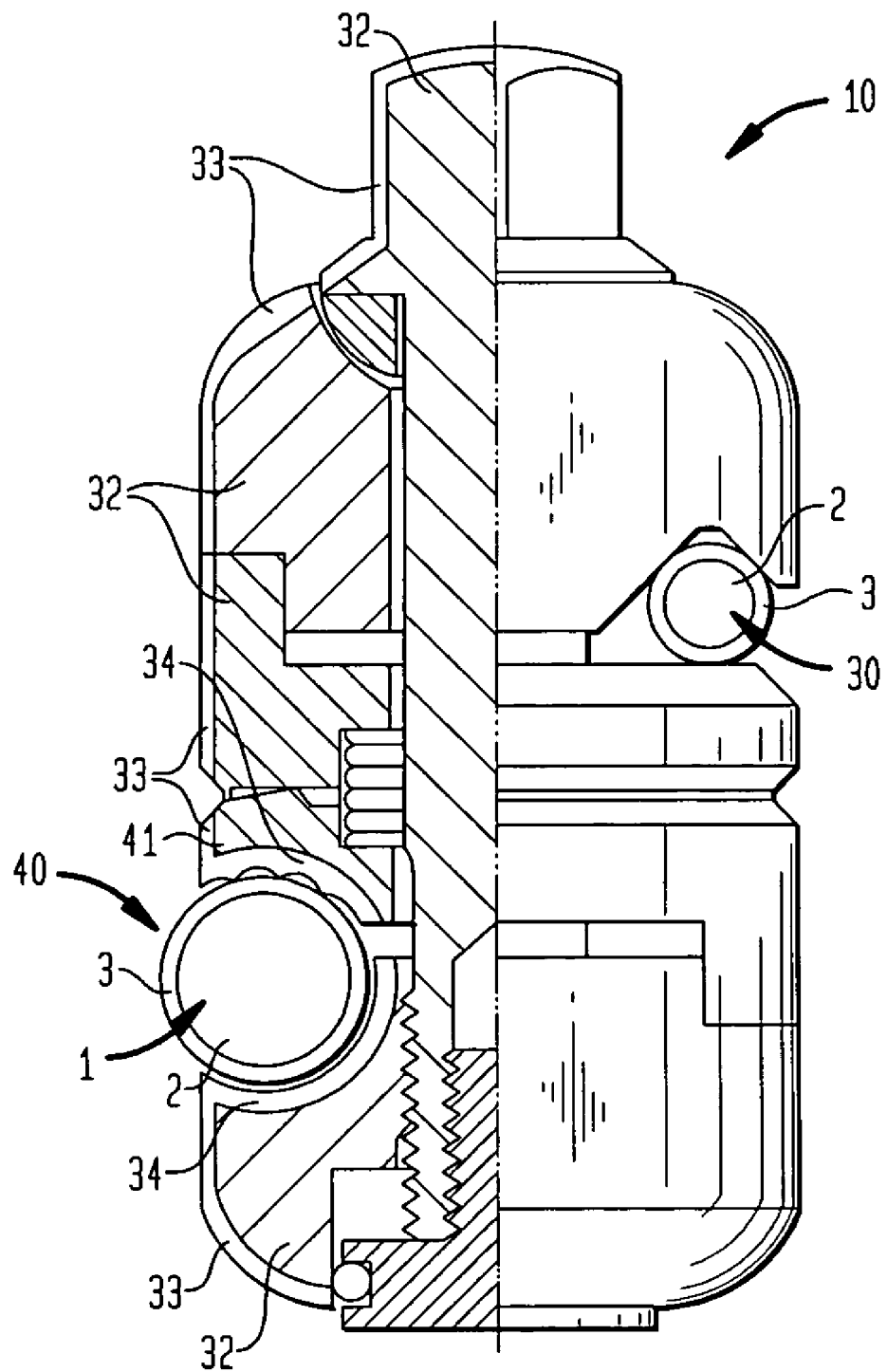
FIG. 3 is a representation of a clamp according to the invention, seen in section in the left and at a lateral view in the right part of the drawing.

Referring to FIG. 3, on the other hand, it is also possible to provide non-conductive clamps 10, e.g. titanium clamp bodies covered at least on the inside with an insulation sheath 34, i.e. around the jaws 40 of the clamp. Preferably, the insulation sheath 33 is also provided on the outside of the clamp.

Both solutions (clamp and/or rod) interrupt the electric loop of the frame and body of a patient and prevent serious induced currents.

A clamp 10 with a non-electrically conductive insulation sheath or covering 34 and 33 is shown in FIG. 3 being a representation of the clamp 10, seen in section in the left and laterally in the right part of the drawing. The elements 32 constituting the core of the clamp 10 can be in carbon fiber or titanium, although the use of aluminum is preferred. The different constituting parts of clamp 10 are known to someone skilled in the art and are explained in U.S. Pat. No. 6,080,153. Sheath 33 and 34 may be of a polymeric material.

In the case that the clamps 10 have on the inner side of the jaws 40 some teeth 41 gripping the outer surface of the sheath 3 of the rod 1, the insulation 34 as shown in FIG. 3 may function in a different way as explained below. Since the rod 1 comprises the core 2 and the sheath 3, the clamp's teeth 41 enter into the sheath 3. The teeth 41 can be made of the core material of the clamp 10 for use with rod 1 which preferably is made of titanium or aluminum and are as such not ferromagnetic, however these materials are conductive. The teeth 41 of the jaws 40 have a length of e.g. 0.3 millimeter, wherein the non-conductive sheath 3 has a radial thickness of e.g. 0.7 millimeter. In this way, it is ensured that the possibly conductive rod core 2 does not come in contact with the conductive teeth 41. The same applies for teeth which would be used to hold the pin 30. However, in other embodiments the insulation sheath 41 may well extend also in the area of the jaws 40.

Referring to FIG. 1, possible stresses on a rod are evaluated. One of the stresses a system may receive is a torsion exerted via two clamps 10, i.e. one end of the rod 1 is rotated around its main axis 5 while the opposite end of the rod 1 is held against rotation or rotated in the opposite direction. If the torque would now be increased until the system breaks there are two possible scenarios of what could happen to a surgeon using the tools. One case, would be that the sheath 3 separates from the core 2 of the rod 1, wherein the teeth 41 of the jaws 40 or the inner surface of the jaws 40 are holding the sheath 3 fast. The second possibility is that the teeth 41 of the jaws 40 of the clamp 10 slide or glide along the circumference of the sheath 3.

According to a preferred embodiment, the rod 1 or pin 30 is designed in such a way that the bond between the sheath and core is strong enough that the clamp 10 will start to glide along the circumference of the sheath 3 before the surfaces between core 2 and sheath 3 separate upon a growing torque. In such a way the rod 1 remains intact in the case that excessive torque stresses are exerted on said rod 1. The same applies in case of tensile forces acting between the sheath and core along the longitudinal axis 5.

The core 2 may be formed with a pultrusion process. Through resin transfer moulding (RTM), a sheath 3 having a known resistivity is molded with the core 2 allowing an interaction between, for example, a carbon fiber core 2 and the sheath 3 at the intermediate surface 6. An improvement to the MRI safe invention relates also to the choice of material and the manner in which that material was applied to the carbon core. A higher modulus carbon fiber is used because the size of the carbon core must be reduced so that once the second material is applied to it, the resulting product has the same size as rods traditionally used by surgeons in external fixation systems. A preferred material for the sheath is VECTRAN® fiber which is preferably braided into a sock and infused with a resin by using a vacuum to pull the resin through the sock. The reduced size, high modulus carbon core can be inserted into a sheath or sock of braided VECTRAN® material with the vacuum being used to pull the resin through the sock. There is an additional heating process step by which the resin is cured. The VECTRAN® material, resin and carbon core are heated to about 160° C. The MRI safe device according to the invention is gamma resistant, non-conductive, non-magnetic, and radiolucent. If gamma resistance is not crucial, KEVLAR® fiber can be used as sheath material. KEVLAR® sheaths have shown to discolor over time, therefore indicating the age of the product. This may be undesirable. With respect to VECTRAN® fiber as choice for the material of the non-conductive sheath part, the thickness of the sheath is important because if it becomes too thick, then it becomes conductive which is an undesirable property.

The core 2 may be non-metallic or metallic conductive or non-conductive. Its main function is to provide stiffness.

The electrical resistivity of the rods 1 or pins 30 shall preferably be greater than 1 kOhm·cm.

The torsional stiffness for rods with 5 mm diameter shall preferably be greater than 0.2 Nm2. The torsional strength for such rods shall preferably be greater than 2 Nm. The bending stiffness for such rods shall preferably be greater than 2.5 Nm2. The bending strength for such rods shall preferably be greater than 15 Nm.

The torsional stiffness for rods with 8 mm diameter shall preferably be greater than 1.5 Nm2. The torsional strength for such rods shall preferably be greater than 11 Nm. The bending stiffness for such rods shall preferably be greater than 20 Nm2. The bending strength for such rods shall preferably be greater than 40 Nm.

The rods 1 are especially MRI safe for the patient when used in any frame configuration for the upper and lower extremities and pelvis, and especially when used in conjunction with Hoffmann II clamps (see U.S. Pat. No. 6,080,153), the assignee's MRI safe product line, wherein the following MRI field parameters apply:

Static field: max. 2 Tesla

Time-varying field: max. 20 Tesla/sec.

Specific absorption rate (SAR): max. 0.4 Watts/kg averaged over the whole body.

A device is considered MRI safe if there is no risk of limb movements due to forces exhibited on the materials of the frame, no risk of nerve or muscle stimulation due to time-varying field and no risk of all body temperature rise greater than 1° C., due to induced current and temperature in the frame being a consequence of the RF field.

It is important to note that any orthopedic frame for external fixation built with the elements described in this application and according to the appended claims can be considered MRI safe irrespective of the position of the frame, i.e. the device can be used for the external fixation of any broken limb of the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fracture fixation system forming a closed loop between bone on first and second sides of the fracture comprising two electrically conductive bone pins having a metallic tip engaging bone at a first end and extending between two external clamps and the respective first and second sides of the bone, a rod element having a unitary anti-magnetic rigid metallic electrically conductive core part and a non-electrically conductive polymeric sheath part covering an exterior surface of the core part extending between the two clamps wherein the anti-magnetic core part is made of titanium or aluminum and the non-electrically conductive sheath part is made of resin material wherein said clamps are electrically conductive and each have at least two jaws having a non-electrically conductive polymeric coated surface formed thereon wherein the jaws have teeth, a length of the teeth of the jaws is smaller in length than a thickness of the insulating sheath of said rod element.

2. The external fixation system as set forth in claim 1 wherein said rod element is a cylindrical rod with a cylindrical sheath.

3. The external fixation system as set forth in claim 1 wherein said rod element is a cylindrical pin with a cylindrical sheath.

4. The external fixation system as set forth in claim 1 wherein said system comprises at least two clamps wherein said jaws engage said rod element.

5. The external fixation system as set forth in claim 1 wherein the core and sheath of a rod or pin hold together upon exertion of a torque around the longitudinal axis of the rod or pin in such a way that the clamp will start to slide along a circumference of the sheath before engaged surfaces between the core and the sheath part separate upon an increasing torque.

6. The external fixation system as set forth in claim 1 further comprising at least two clamps for engaging said rod element, said clamps made of an electrically conductive non-ferromagnetic material, said at least two clamps having a non-electrically conducting polymeric insulation covering.

7. A MRI safe external bone fracture fixation system comprising:
   at least two electrically conductive bone pins having a metallic tip engaging bone at a first end;
   at least two clamps made of an electrically conductive non-ferromagnetic metallic material for clamping second ends of respective bone pins of the at least two pins located outside the body, said clamps having a non-electrically conductive polymeric insulation covering; and
   at least one cylindrical rod captured by and extending between said clamps, said rod made from a single piece non-ferromagnetic rigid electrically conductive metallic material core surrounded by a non-electrically conductive polymeric sheath wherein the clamp comprises jaws having teeth, wherein the length of the teeth of the jaws is smaller than the thickness of the non-electrically conductive sheath of said rod.

8. The external fixation system as set forth in claim 7 wherein said system comprises at least two clamps wherein said jaws engage said rod and said pin.

9. The external fixation system as set forth in claim 7 wherein the core and sheath form a rod or pin with the core and sheath together upon exertion of a torque around the longitudinal axis of the rod or pin in such a way that the clamp will start to slide along a circumference of the sheath before engagement surfaces between core and sheath separate upon an increasing torque.

10. The external fixation system as set forth in claim 7 wherein said core comprises aluminum.

11. The external fixation system as set forth in claim 7 wherein the rod core is made of a non-magnetic metal and the sheath is made from an electric insulation material, the sheath being bonded to an outer circumferential core surface.

12. The external fixation system as set forth in claim 11 wherein the core is made of titanium.

13. An external fixation system comprising an electrically conductive pin having a metallic tip for engaging bone and a rod element with a core body having an electrically conductive anti-magnetic metallic core part and a non-electrically conductive carbon fiber reinforced polymeric sheath covering an exterior surface of the metallic core part, and at least two clamps each comprising at least two jaws having teeth, each jaw having a polymeric coating, wherein said jaws engage said rod, wherein a length of teeth of the jaws of any clamp is smaller than a thickness of the insulating sheath of said at wherein the core and sheath of a rod hold together upon exertion of a torque around the longitudinal axis of the rod in such a way that the clamp will start to slide along a circumference of the sheath before engaged surfaces between the core and the carbon fiber sheath part separate upon an increasing torque.

14. The external fixation system as set forth in claim 13 wherein the anti-magnetic core part is made of electrically conductive titanium or aluminum and the non-conductive sheath part is made of resin material.

15. The external fixation system as set forth in claim 14 wherein the anti-magnetic core part is made of carbon fiber and the non-conductive sheath part is made of co-extruded resin material within a resin transfer molding process.

16. The external fixation system as set forth in claim 13 wherein said rod element is a cylindrical rod with a cylindrical sheath.

17. The external fixation system as set forth in claim 13 wherein said rod element is a cylindrical pin with a cylindrical sheath.

18. A MRI safe external fixation system comprising:
   at least two rod clamps made of an electrically conductive non-ferromagnetic material, said clamps each having two pairs of jaw members with a non-electrically conductive polymeric insulation covering; and
   at least one cylindrical rod captured by a pair of jaws and extending between said rod clamps, said rod made from a single non-ferromagnetic rigid electrically conductive material core surrounded by a non-electrically conductive sheath and at least two electrically conductive bone pins having metallic first ends engaging bone and second ends each engaging one pair of clamp jaws.

19. The external fixation system as set forth in claim 18 wherein the jaws have teeth.

20. The external fixation system as set forth in claim 19 wherein said system comprises at least one clamp wherein said jaws engage said rod and a pin.

21. The external fixation system as set forth in claim 20 wherein the length of the teeth of the jaws of any clamp is smaller than the thickness of the non-electronically conductive sheath of said at least one rod or pin.

22. The external fixation system as set forth in claim 21 wherein the core and sheath form a rod or pin with the core and sheath together upon exertion of a torque around the longitudinal axis of the rod or pin in such a way that the clamp will start to slide along a circumference of the sheath before engagement surfaces between core and sheath separate upon an increasing torque.

23. The external fixation system as set forth in claim 22 wherein said core comprises aluminum.

24. The external fixation system as set forth in claim 18 wherein the rod core is made of a non-magnetic metal and the sheath is made from an electric insulation material, the sheath being bonded to an outer circumferential core surface.

25. The external fixation system as set forth in claim 24 wherein the core is made of titanium.

* * * * *

UNITED STATES PATENT AND TRADEMARK OFFICE
CERTIFICATE OF CORRECTION

PATENT NO. : 7,527,626 B2
APPLICATION NO. : 10/959340
DATED : May 5, 2009
INVENTOR(S) : Christian Lutz et al.

It is certified that error appears in the above-identified patent and that said Letters Patent is hereby corrected as shown below:

Column 1, line 7, "make use" should read --make the use--.
Column 1, line 13, "with a MRI" should read --with an MRI--.
Column 1, line 21, "not to be made" should read --not be made--.
Column 1, line 35, "either along or" should read --either alone or--.
Column 1, line 60, "a MRI system" should read --an MRI system--.
Column 2, line 11, "acts an electrical" should read --acts as an electrical--.
Column 2, line 54, "pins 30 are" should read --pins 30 is--.
Column 3, line 38, "One case, would" should read --One case would--.
Column 5, line 30, "A MRI" should read --An MRI--.
Column 6, line 29, "A MRI" should read --An MRI--.

Signed and Sealed this

Twenty-second Day of June, 2010

David J. Kappos
*Director of the United States Patent and Trademark Office*